(12) United States Patent
Chrisochoou et al.

(10) Patent No.: US 6,531,623 B2
(45) Date of Patent: Mar. 11, 2003

(54) CONTINUOUS PROCESS FOR PRODUCING CARBONIC ACID DIARYL ESTER

(75) Inventors: Andreas Chrisochoou, Köln (DE); Steffen Kühling, Meerbusch (DE); Johan Vanden Eynde, Zwijnaarde (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/028,602

(22) Filed: Dec. 19, 2001

(65) Prior Publication Data

US 2002/0087022 A1 Jul. 4, 2002

(30) Foreign Application Priority Data

Dec. 21, 2000 (DE) ........................................ 100 63 869

(51) Int. Cl.$^7$ .............................................. C07C 69/96
(52) U.S. Cl. ...................................... 558/274; 558/260
(58) Field of Search ................................. 558/260, 274

(56) References Cited

U.S. PATENT DOCUMENTS 3,017,424 A * 1/1962 Meyer et al.
4,016,190 A   4/1977 Böckmann et al. ......... 260/463
4,697,034 A * 9/1987 Janatpour et al.
5,710,310 A * 1/1998 Ooms et al.

OTHER PUBLICATIONS

Chemistry and Physics of Polycarbonates, Polymer Reviews, H.Schnell, vol. 9, John Wiley and Sons Inc. (month unavailable), 1964, pp. 50–51.

* cited by examiner

Primary Examiner—Deborah D. Carr
Assistant Examiner—Paul A. Zucker
(74) Attorney, Agent, or Firm—Joseph C. Gil; Aron Preis

(57) ABSTRACT

A two stage interfacial polycondensation process for the production of carbonic acid diaryl ester is disclosed. The invention concerns an improvement to the process that entails forming in a first stage a reaction mixture that contains an inert solvent, at least one monophenol, phosgene, and aqueous alkali hydroxide solution, passing said reaction mixture to a second stage through at least one constriction at a velocity of 3 to 15 m/s under conditions designed to expose the mixture to a pressure drop of 0.1 to 2.5 bar, and in said second stage passing said mixture through at least one dispersing element at a velocity of 2 to 10 m/s under conditions designed to expose the mixture to a pressure drop of 0.1 to 0.5 bar. The resulting product is characterized by its purity and suitability for the manufacture of polycarbonates in the melt transesterification process.

7 Claims, No Drawings

CONTINUOUS PROCESS FOR PRODUCING CARBONIC ACID DIARYL ESTER

FIELD OF THE INVENTION

The present invention relates to a new process for producing carbonic acid diaryl esters in which the carbonic acid diaryl esters are produced by reacting monophenols and phosgene in an inert solvent in the presence of alkali and a nitrogen catalyst in the interfacial process.

SUMMARY OF THE INVENTION

A two stage interfacial polycondensation process for the production of carbonic acid diaryl ester is disclosed. The invention concerns an improvement to the process that entails forming in a first stage a reaction mixture that contains an inert solvent, at least one monophenol, phosgene, and aqueous alkali hydroxide solution, passing said reaction mixture to a second stage through at least one constriction at a velocity of 3 to 15 m/s under conditions designed to expose the mixture to a pressure drop of 0.1 to 2.5 bar, and in said second stage passing said mixture through at least one dispersing element at a velocity of 2 to 10 m/s under conditions designed to expose the mixture to a pressure drop of 0.1 to 0.5 bar. The resulting product is characterized by its purity and suitability for the manufacture of polycarbonates in the melt transesterification process.

BACKGROUND OF THE INVENTION

The production of carbonic acid diaryl esters by the interfacial process is basically known from the literature, cf. Chemistry and Physics of Polycarbonates, Polymer Reviews, H. Schnell, Vol.9, John Wiley and Sons, Inc. (1964), p. 50/51). It is known to a person skilled in the art and described in the above-mentioned literature and, for example, in U.S. Pat. No. 4,016,190, that thorough mixing of the two phases is required for reaction progress. However, satisfactory results with respect to yield and purity, in particular the chloroformic acid aryl ester content of the carbonic acid diaryl ester obtained are not always achieved with the known processes. Starting from the state of the art, in particular U.S. Pat. No. 4,016,190, the object was to provide a process which allows better yields and purities of carbonic acid diaryl ester. It is particularly important to avoid entraining the chloroformic acid aryl ester into the end product as this compound interferes during the melt transesterification process to form the polycarbonate.

DETAILED DESCRIPTION OF THE INVENTION

It has now surprisingly been found that, during the continuous production of carbonic acid diaryl esters by reaction of monophenols and phosgene in an inert solvent in the presence of alkali in the interfacial polycondensation process (herein interfacial process) it is necessary to maintain specific mixing conditions in order to achieve an optimum reaction in short reaction times with high yields and satisfactory purities of the carbonic acid diaryl ester at low temperatures.

It has also been found that a mixing range which is optimum in each case exists as a function of the progress of the reaction stage.

The alkali used may be a lye solution (that is an aqueous solution of any of Na, K, Li, or Ca-hydroxide), preferably sodium hydroxide solution, and is preferably used as a 20 to 55 wt. %, particularly preferably 30 to 50 wt. % solution in the process according to the invention.

Phosgene may be used in liquid or gaseous form or dissolved in the inert solvent.

Suitable monophenols for use in the reaction include phenols of formula (I)

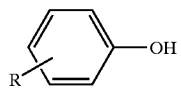

(I)

wherein
R is hydrogen, tert.-butyl, halogens or a branched or unbranched $C_8$ and/or $C_9$ alkyl radical,
therefore phenol itself, alkylphenols such as cresols, p-tert.-butylphenol, p-cumylphenol, p-n-octylphenol, p-iso-octylphenol, p-n-nonylphenol and p-iso-nonylphenol, halogen phenols such as p-chlorophenol, 2,4-dichlorophenol, p-bromophenol and 2,4,6-tribromophenol may be used. Phenol is preferred.

Inert organic solvents used in the process include, for example, dichloromethane, toluene, the various dichloroethanes and chloropropane compounds, chlorobenzene and chlorotoluene, dichloromethane preferably being used.

Reaction control is preferably carried out continuously and preferably in a plug flow without significant back-mixing. This may be effected, for example, in tubular reactors. Reaction control is split into two successive stages.

In the first stage, the aqueous phase is mixed with the organic phase in a diaphragm, a nozzle or a dynamic mixer. It is preferable to use a nozzle, for example a combined confuser/diffuser provided with apertures or an abruptly tapered tube.

In said first stage the aqueous phase flows through the apertures at velocities between 2 and 15 m/s, preferably between 6 and 12 m/s. The pressure drop varies between 0.1 and 2.5 bar, preferably between 0.5 and 1.5 bar. In the narrowest cross-section the mixture has a velocity of between 2 and 15 m/s and a pressure drop of between 0.1 and 2 bar.

The reaction takes place in a reactor that is equipped with cooling means, preferably a liquid distributor, to cool the reaction mixture to a temperature lower than 50° C., preferably lower than 40° C., downstream of the mixing elements.

The mixing conditions in the first and second stage of reaction ensure high phosgene yields, high-purity carbonic acid diaryl ester, prevent high concentrations of the chloroformic acid aryl ester intermediate product in the end product and require but short reaction times. With lower mixing performance, the reaction is incomplete, i.e. the monophenol has not reacted fully with the phosgene so, on the one hand, monophenol passes into the waste water and, on the other hand, the intermediate product of the chloroformic acid aryl ester is entrained into the end product. A high saponification cleavage and back-cleavage of the phosgene and carbonic acid diaryl ester occurs with excessively high mixing performances, so, on the one hand, monophenol passes into the waste water and, on the other hand, a much higher excess of phosgene is required.

During the reaction in the first stage, the reaction components are initiated by combining the educts phosgene, inert solvent, which preferably serves only as solvent for the phosgene, and phenol, which has preferably already been dissolved beforehand in the caustic solution. The residence time in the continuous process of the first stage is in the range of 2 seconds to 300 seconds, preferably in the range of 4 seconds to 200 seconds. The pH of the first stage is preferably adjusted by the ratio of caustic/phenol/phosgene so the pH lies in the range of 11.0 to 12.0, preferably 11.2 to 11.8.

In the second stage of the continuous process, the reaction is completed to form the carbonic acid diaryl ester. Thorough mixing of the two phases (aqueous and organic phase) in the second stage is carried out by preferably static or dynamic dispersing elements located at regular distances. Preferred static elements include diaphragms, nozzles or constricted tubular cross-sections. Fittings (static mixers) may also be inserted therein to distribute and mix the flow. The pressure drop per dispersing element is preferably between 0.1 and 0.5 bar. The velocity in the narrowest cross-section of the element is typically between 2 and 10 m/s, preferably between 3 and 9 m/s, quite particularly preferably between 4 and 7 m/s. The mixing time (residence time in the dispersing element) is less than 0.5 s, preferably between 0.01 and 0.1 s. The residence time between two successive dispersing elements is between 3 and 12 s, preferably between 5 and 10 s.

The residence times of the second stage in the process according to the invention are between 1 minute and 30 minutes, preferably between 2 minutes and 20 minutes, quite particularly preferably between 3 minutes and 15 minutes.

Suitable dynamic mixers include, for example, pumps or generally rotor/stator systems.

In a preferred embodiment, a catalyst is supplied at the beginning of the second stage. The reaction of the process is preferably cooled directly after or during addition of the catalyst. The reaction temperature is kept <50° C., preferably <40° C., quite particularly preferably <35° C. by cooling. It may be advantageous to add the catalyst at a plurality of, preferably two, points of the second stage of the reaction in the continuous process.

Intermediate buffering may also be carried out between the first and second stage while maintaining the mixed phases.

The catalysts to be used according to the invention are tertiary amines, N-alkyl piperidines or onium salts. Onium salts in the present application are interpreted as compounds such as $NR_4X$, wherein R is an alkyl and/or aryl radical and/or an H and X is an anion. Tributylamine, triethylamine and N-ethylpiperidine are preferably used. N-ethylpiperidine is quite particularly preferred. The concentrations of the catalysts are 0.0001 mol % to 0.1 mol %, preferably 0.01 mol % to 0.075 mol %, based on the phenol used.

In the process according to the invention, the content of chloroformic acid aryl ester in the resultant carbonic acid diaryl ester is <2 ppm, preferably <0.5 ppm.

The pH is preferably regulated in the second stage of the process by measuring the pH (which is preferably measured online in the continuous process) and corresponding adjustment of the pH by addition of the caustic solution. The quantity of caustic solution supplied is adjusted in such a way that the pH lies in the range of 7.5 to 10.5, preferably 8 to 10 after the second stage of the process.

In the process according to the invention, phosgene is supplied in a ratio of 1.01 to 1.14 mol %, preferably 1.05 to 1.10 mol %, based on the phenol. The solvent is added in such a way that the carbonic acid diphenyl ester exists in a 5 to 60% solution, preferably 20 to 45% solution after the reaction.

After the reaction, the organic phase containing the carbonic acid diaryl ester is usually washed with an aqueous liquid and separated as far as possible from the aqueous phase after each washing procedure. Washing is preferably carried out with de-ionized water. The carbonic acid diaryl ester solution is usually cloudy after washing and separation of the washing liquid. Aqueous liquids, for example dilute mineral acids such as HCl or $H_3PO_4$ are used to separate the catalyst and water which is completely de-ionized is used for further purification. The concentration of HCl or $H_3PO_4$ in the washing liquid may be, for example, 0.5 to 1.0 wt. %. The organic phase is preferably washed twice by way of example.

Basically known separating vessels, phase separators, centrifuges or coalescers or also combinations of these devices may be used as phase-separating devices for separating the washing liquid from the organic phase.

The solvent is evaporated to obtain the high-purity carbonic acid diester. Evaporation may be carried out in a plurality of evaporator stages. For example, it is carried out through one or more successive distillation columns in which the solvent is separated from the carbonic acid diaryl ester.

This purification stage or stages may be conducted, for example, continuously in such a way that the bottom temperature during distillation is >150° C. to 310° C., preferably >160 to 230° C. The pressures required to carry out these distillation processes are between 1 and 1000 mbar, preferably between 5 and 100 mbar.

The resultant carbonic acid diesters are characterized/distinguished by very high purity with GC purities (cool on column method) >99.99%, preferably 99.9925%, quite particularly preferably >99.995% and extremely good transesterification behaviour, so a polycarbonate of excellent quality may be produced.

The production of aromatic oligo/polycarbonates by the melt transesterification process is known from the literature and has already been described, for example, in the Encyclopedia of Polymer Science, Vol. 10 (1969), Chemistry and Physics of Polycarbonates, Polymer Reviews, H. Schnell, Vol 9, John Wiley and Sons, Inc. (1964) or U.S. Pat. No. 5,340,905.

EXAMPLES

Example 1

A mixture of 117 kg/h completely de-ionized water with 48 kg/h 50% NaOH and 54.9 kg/h phenol is continuously combined with a solution of 98 kg/h methylene chloride and 31.2 kg/h phosgene (8 mol % excess, based on phenol) in a cooled tubular reactor. The two phases are mixed in a confuser/diffuser nozzle provided with apertures. The pressure drop in the aqueous phase (orifice side) is 0.8 bar at a flow rate of 9 m/s. The pressure drop in the organic phase is 0.1 bar. After an average residence time of 15 seconds, 6.5 kg/h 50% NaOH are accordingly added to this reaction mixture in the second stage of the process and 1.1 kg/h (0.9% in methylene chloride) of the catalyst N-ethylpiperidine are added directly afterwards and the reaction mixture immediately cooled to 30° C. The reaction mixture is then mixed constantly by flowing through of a pipe provided with constrictions. The velocities in the constrictions are 4 m/s (beginning of pipe) and 6 m/s (end of pipe) with corresponding pressure drops of 0.15 bar and 0.30 bar per dispersing element and a residence time in the constrictions of 0.025 to 0.040 s. The residence time between the successive constrictions is 9 s in each case. The total residence time is about 300 seconds. The organic phase is subsequently separated from the aqueous phase. After washing with 0.6% HCl and water and final phase separation, a 99.996% (GC method, cool on column method) diphenylcarbonate is obtained after evaporation of the methylene chloride. The chloroformic acid phenyl ester content is <0.5 ppm. The DPC is very well suited for use in the melt transesterification process.

Comparison Example 1

As example 1, but the two phases are mixed by a confuser/diffuser nozzle of a different design so the velocity is only 1.5 m/s with a pressure drop of 20 m bar. After washing with 0.6% HCl and water and final phase separation, a 99.85% (GC method, cool on column method) diphenylcarbonate is obtained after evaporation of the methylene chloride. The chloroformic acid phenyl ester content is 1,500 ppm. The DPC is not suitable for use in the melt transesterification process.

Example 2

As example 1, but the velocities in the constrictions in the second stage of the process are only 1 m/s (beginning of pipe) and 1.5 m/s (end of pipe) with corresponding drops in pressure of 0.010 bar and 0.020 bar per dispersing element and a residence time in the connections of 0.08 to 0.10 s.

After washing with 0.6% HCl and water and final phase separation, a 99.85% (GC method, cool on column method) diphenyl carbonate is obtained after evaporation of the methylene chloride. The chloroformic acid phenyl ester content is 350 ppm. The DPC is not suitable for use in the melt transesterification process.

Comparison Example 3

As example 1 but the velocities in the constrictions in the second stage of the process are 8 m/s (beginning of pipe) and 11.5 m/s (end of pipe) with drops in pressure of 0.6 bar and 1.2 bar per dispersing element and corresponding residence times of 0.015 to 0.020 s in the constrictions. To achieve the same DPC yield, i.e. almost complete conversion of the phenol, 33.8 kg/h phosgene (17 mol % excess based on phenol) are now required.

After washing with 0.6% HCl and water and final phase separation, a 99.995% (GC method, cool on column method) diphenyl carbonate is obtained after evaporation of the methylene chloride. The chloroformic acid phenyl ester content is <0.5 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In the interfacial polycondensation process for the production of carbonic acid diaryl ester the improvement comprising forming in a first stage a reaction mixture that contains an inert solvent, at least one monophenol, phosgene, and aqueous alkali hydroxide solution, passing said reaction mixture through at least one constriction at a velocity of 3 to 15 m/s under conditions designed to expose the mixture to a pressure drop of 0.1 to 2.5 bar, and in the second stage passing said mixture through at least one dispersing element at a velocity of 2 to 10 m/s under conditions designed to expose the mixture to a pressure drop of 0.1 to 0.5 bar.

2. The process of claim 1 wherein the residence time of the reaction mixture in the first stage is in the range of 2 seconds to 300 seconds.

3. The process of claim 1 wherein the pH of the reaction mixture in the first stage is in the range of 11.0 to 12.0.

4. The process of claim 1 wherein second stage is carried out in a reactor equipped with a plurality of elements to distribute and mix said mixture.

5. The process of claim 4 wherein the residence time per element is less than 0.5 second.

6. The process of claim 5 wherein the residence time between two successive elements is 3 to 12 seconds.

7. The process of claim 1 wherein residence time in the second stage is 1 to 30 minutes.

* * * * *